(12) United States Patent
Okubo et al.

(10) Patent No.: US 6,696,540 B2
(45) Date of Patent: Feb. 24, 2004

(54) EPISULFIDE COMPOUND, METHOD FOR PRODUCING THE SAME AND OPTICAL PRODUCT COMPRISING THE SAME

(75) Inventors: Tsuyoshi Okubo, Tokyo (JP); Ken Takamatsu, Tokyo (JP)

(73) Assignee: Hoya Corporation, Tokyo (JP)

( * ) Notice: Subject to any disclaimer, the term of this patent is extended or adjusted under 35 U.S.C. 154(b) by 0 days.

(21) Appl. No.: 10/299,685

(22) Filed: Nov. 20, 2002

(65) Prior Publication Data

US 2003/0144431 A1 Jul. 31, 2003

(30) Foreign Application Priority Data

Nov. 28, 2001  (JP) ......................................... 2001-362375

(51) Int. Cl.$^7$ ............................................... C08G 18/38
(52) U.S. Cl. ...................... 528/76; 528/109; 528/377; 528/378; 528/392; 549/15; 549/18; 549/19; 549/24
(58) Field of Search .............................. 549/15, 18, 19, 549/24; 528/76, 109, 377, 378, 392

(56) References Cited

FOREIGN PATENT DOCUMENTS

| EP | 0785 194 A1 | 7/1997 |
|----|----|----|
| JP | 58-164615 | 9/1983 |
| JP | 60-199016 | 10/1985 |
| JP | 02-270859 | 11/1990 |
| JP | 03-236386 | 10/1991 |
| JP | 05-148340 | 6/1993 |
| JP | 07-118390 | 5/1995 |
| JP | 09-071590 | 3/1997 |
| JP | 09-110979 | 4/1997 |
| WO | WO 02/23230 A1 | 3/2002 |

OTHER PUBLICATIONS

Rinzema, L.C. et al., Orthothioesters and 1,1–Bis–(Ethylthio)–1–Alkenes (Thioacetals of Ketenes), Recl. Trav. Chim. Pays–Bas, No. 78, pp. 354–363 (1959).

Matlack, et al., Alkyl–Substituted s–Trithianes Containing Functional Groups in the Side Chain, J. Org. Chem., vol. 26, pp. 1455–1460 (1961).

European Search Report dated Dec. 17, 2002.

*Primary Examiner*—Robert Dawson
*Assistant Examiner*—D. Aylward
(74) *Attorney, Agent, or Firm*—Finnegan, Henderson, Farabow, Garrett & Dunner, LLP

(57) ABSTRACT

An episulfide compound useful as a starting material for optical materials that have a high refractive index and a high Abbe's number is provided. A method for producing the same and an optical product made with the same are also provided. The episulfide compound may be represented by the general formula (1):

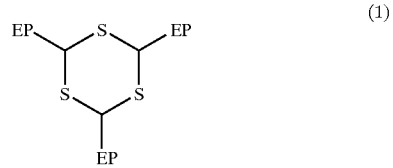

(1)

wherein EP represents

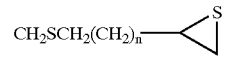

and n is an integer of from 0 to 2. A method for producing the episulfide compound represented by the general formula (1) may involve reacting a mercapto group-containing episulfide compound with 2,4,6-trimethylene-1,3,5-trithiane.

17 Claims, No Drawings

EPISULFIDE COMPOUND, METHOD FOR PRODUCING THE SAME AND OPTICAL PRODUCT COMPRISING THE SAME

CROSS-REFERENCE TO RELATED APPLICATION

The present application claims priority under 35 U.S.C. § 119 of Japanese Application No. 2001-362375, filed Nov. 28, 2001, the disclosure of which is expressly incorporated by reference herein in its entirety.

DESCRIPTION

1. Field of the Invention

The present invention relates to an episulfide compound, a method for producing the same, and an optical product made with the same. Generally, the invention relates to an episulfide compound that may give optical materials having a high refractive index and a high Abbe's number and having excellent heat resistance and transparency, to a method for producing the same, and to an optical product made with the same.

2. Background of the Invention

Plastics are used for various optical applications these days, for example, for lenses and others, as being lightweight, difficult to break, and easily colored when compared with glass. Optical plastic materials include poly (diethylene glycol bisallylcarbonate) (CR-39) and poly (methyl methacrylate). These plastics, however, have a refractive index of 1.50 or less. Therefore, for example, when they are used for lens materials, the lenses produced need to be thicker for increased power, and they lose the advantage of being lightweight. In particular, powerful concave lenses are thick at their periphery, and are therefore unfavorable as causing birefringence and chromatic aberration. For spectacles, such thick lenses are often not aesthetic. To obtain thin lenses, materials with higher refractive index may be used. In general, the Abbe's number of glass and plastics decreases with the increase in their refractive index, and, as a result, their chromatic aberration increases. Accordingly, plastic materials having a high refractive index and a high Abbe's number are desired.

Plastic materials proposed as having such properties include, for example, (1) polyurethanes obtained through addition-polymerization of a polythiol having bromine in the molecule and a polyisocyanate (Japanese Patent Laid-Open No.164615/1983); and (2) polythiourethanes obtained through addition-polymerization of a polythiol and a polyisocyanate (Japanese Patent Publication No. 58489/1992 and Japanese Patent Laid-Open No.148340/1993). For the starting material, polythiol for the polythiourethanes of above (2), may be branched polythiols having an increased sulfur content (Japanese Patent Laid-Open Nos. 270859/1990 and 148340/1993), and polythiols into which is introduced a dithiane structure for increasing their sulfur content (Japanese Patent Publication No. 5323/1994 and Japanese Patent Laid-Open No.118390/1995). Other plastic materials proposed as having such properties include (3) polymers of an alkyl sulfide having a polymerization-functional group, episulfide (Japanese Patent Laid-Open Nos. 71580/1997 and 110979/1997).

However, though their refractive index is increased a little, the polyurethanes of above (1) still have a low Abbe's number and have some other drawbacks in that their light-fastness is poor, their specific gravity is high and, therefore, they are not lightweight. Of the polythiourethanes (2), those for which the starting polythiol used has a high sulfur content have an increased refractive index of from about 1.60 to 1.68, but their Abbe's number is lower than that of optical inorganic glass having a refractive index on the same level. Therefore, they still have a problem in that their Abbe's number must be increased more. On the other hand, one example of the alkyl sulfide polymers (3) having an Abbe's number of 36 has an increased refractive index of 1.70. The lenses obtained by using this polymer can be extremely thin and lightweight. However, plastic materials with high Abbe's number and refractive index are still desired.

SUMMARY OF THE INVENTION

The present invention has been made to address the problems noted above. The present invention provides compounds that may give optical materials having a high refractive index and a high Abbe's number and having excellent heat resistance and transparency, a method for producing the same, and an optical product made with the same.

The present inventors have determined that compounds of 1,3,5-trithiane (hereinafter abbreviated as "trithiane") with an episulfide derivative bonded thereto are useful in solving the above-noted problems, and that the compounds may be efficiently produced in a specific method. Specifically, the invention provides an episulfide compound represented by the general formula (1):

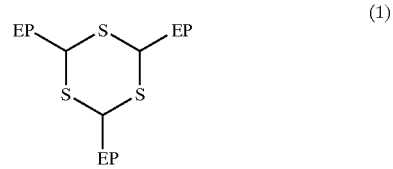

(1)

wherein EP represents

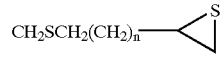

and n is an integer of from 0 to 2. The invention also provides a method for producing an episulfide compound represented by the general formula (1) by reacting a mercapto group-containing episulfide compound with 2,4,6-trimethylene-1,3,5-trithiane.

DESCRIPTION OF THE INVENTION

The particulars shown herein are by way of example and for purposes of illustrative discussion of the various embodiments of the present invention only. In this regard, no attempt is made to show details of the invention in more detail than is necessary for a fundamental understanding of the invention, the description making apparent to those skilled in the art how the several forms of the invention may be embodied in practice.

Unless otherwise stated, a reference to a compound or component, includes the compound or component by itself, as well as in combination with other compounds or components, such as mixtures of compounds.

The episulfide compound of the invention is represented by the general formula (1) mentioned below, from which it is seen that the compounds have three, optionally identical, episulfide-containing substituents bonded to the trithiane ring thereof.

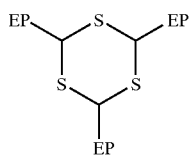

(1)

wherein EP represents

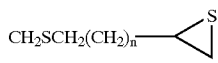

and n is an integer of from 0 to 2.

The trithiane ring of the episulfide compound represented by the general formula (1) has a high sulfur content, in which the atomic refraction is high and which therefore significantly increases the refractive index of the polymers obtained by using the episulfide compound of the invention. In addition, the ethylene sulfide chain to be formed through ring-cleavage polymerization of the episulfide compound also contributes toward increasing the refractive index of the polymers. In general, the Abbe's number of amorphous materials is apt to decrease with the increase in the refractive index thereof. One problem with polymers having high sulfur content is that the electron resonance of sulfur is remarkable, therefore often significantly reducing the Abbe's number. However, the episulfide compounds of the invention are free from this problem. Another cause of the increase in the refractive index is the decrease in the molar volume thereof. This is often seen in polymers having a high crosslinking density and a strong intermolecular force. The episulfide compound of the invention has three polymerization-functional groups, and the refractive index of its polymers is increased especially by the former effect. In the general formula (1), the increase in the number n lowers the sulfur content and the crosslinking density, therefore giving polymers having a reduced refractive index. Accordingly, n is generally in a range of from 0 to 2. In addition, since the glass transition temperature (Tg) of the polymers obtained by using the episulfide compound of the invention lowers with the increase in n in the general formula (1), n is generally in a range of from 0 to 2 in order to obtain polymers having good heat resistance.

For example, the episulfide compound represented by the general formula (1) of the invention includes 2,4,6-tris(epithiomethylthiomethyl)-1,3,5-trithiane, 2,4,6-tris(epithioethylthiomethyl)-1,3,5-trithiane, and 2,4,6-tris(epithiopropylthiomethyl)-1,3,5-trithiane.

These episulfide compounds of the invention may be efficiently produced according to the method of the invention by reacting 2,4,6-trimethylene-1,3,5-trithiane having a methylene group introduced into its 2,4,6-positions, with a mercapto group-containing episulfide compound at the methylene group of the trithiane through ene-thiol reaction.

The mercapto group-containing episulfide compound includes 3-mercaptopropene sulfide, 4-mercaptobutene sulfide, and 5-mercaptopentene sulfide. For example, 3-mercaptopropene sulfide may be prepared according to the method described in F. P. Doyle et al., *Journal of Chemical Society*, p. 2660 (1960).

The method for producing the episulfide compound of the invention may comprise the following steps:

(a) reacting chloroacetaldehyde with hydrogen sulfide to obtain 2,4,6-tris(chloromethyl)-1,3,5-trithiane;

(b) adding a base to the product obtained in step (a) to remove hydrogen chloride to obtain 2,4,6-trimethylene-1,3,5-trithiane; and (c) reacting the 2,4,6-trimethylene-1,3,5-trithiane with 3-mercaptopropene sulfide/4-mercaptobutene sulfide/5-mercaptopropentene sulfide in the presence of a radical generator to obtain the episulfide compound.

One typical example of the method for producing an episulfide compound of the invention, 2,4,6-tris(epithiomethylthiomethyl)-1,3,5-trithiane (a compound of the general formula (1) wherein n is 0), is shown as Scheme 1 mentioned below. An aqueous 40 wt. % chloroacetaldehyde solution is dissolved in 70 wt. % sulfuric acid, and hydrogen sulfide is introduced thereinto at −20 to 40° C. for 2 to 100 hours to give 2,4,6-tris(chloromethyl)-1,3,5-trithiane. Alternatives to sulfuric acid as the acidic solvent include any of 60/40 (v/v) 95 wt. % sulfuric acid-acetic acid, or hydrogen sulfide-saturated acetic acid, ether, or 95 wt. % ethanol. To the resulting methanol solution of the thus-formed chlorine compound is added potassium hydroxide with which the chlorine compound is processed at −10 to 40° C. for 0.5 to 10 hours for removal of hydrogen chloride from it to give 2,4,6-trimethylene-1,3,5-trithiane. This is thermally reacted with 3-mercaptopropene sulfide at 0 to 100° C. for 6 to 100 hours in the presence of a radical generator (described below), to obtain the intended product, 2,4,6-tris(epithiomethylthiomethyl)-1,3,5-trithiane.

The radical generator may be any of azobisbutyronitrile, benzoyl peroxide, or bis(cyclohexylcarbonyl) peroxide.

Alternatives to 3-mercaptopropene sulfide as the mercapto group-containing episulfide compound include 4-mercaptobutene sulfide and 5-mercaptopentene sulfide, and these give 2,4,6-tris(epithioethylthiomethyl)-1,3,5-trithiane and 2,4,6-tris(epithiopropylthiomethyl)-1,3,5-trithiane, respectively.

Scheme 1:

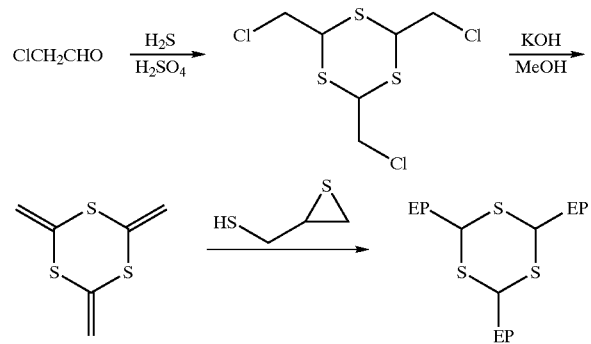

wherein EP represents

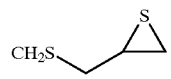

and Me is a methyl group.

Next, are described optical materials obtained by using the episulfide compound of the invention. The episulfide compound represented by the general formula (1) is a component, and it may be used either singly or in admixture of two or more thereof. Further, the episulfide compound may contain any other optional component including other episulfide compounds, epoxy compounds, and homopolymerizable vinyl monomers, for suitably improving the properties of the polymers to be obtained.

Examples of the optional episulfide compounds are linear organic compounds such as bis(β-epithiopropylthio)methane, 1,2-bis(β-epithiopropylthio)ethane, 1,3-bis(β-epithiopropylthio)propane, 1,2-bis(β-epithiopropylthio)propane, 1-(β-epithiopropylthio)-2-(β-epithiopropylthiomethyl)propane, 1,4-bis(β-epithiopropylthio)butane, 1,3-bis(β-epithiopropylthio)butane, 1-(β-epithiopropylthio)-3-(β-epithiopropylthiomethyl)butane, 1,5-bis(β-epithiopropylthio)pentane, 1-(β-epithiopropylthio)-4-(β-epithiopropylthiomethyl)pentane, 1,6-bis(β-epithiopropylthio)hexane, 1-(β-epithiopropylthio)-5-(β-epithiopropylthiomethyl)hexane, 1-(β-epithiopropylthio)-2-[(2-β-epithiopropylthioethyl)thio]ethane, and 1-(β-epithiopropylthio)-2-[[2-(2-β-epithiopropylthioethyl)thioethyl]thio]ethane; branched organic compounds such as tetrakis(β-epithiopropylthiomethyl)methane, 1,1,1-tris(β-epithiopropylthiomethyl)propane, 1,5-bis(β-epithiopropylthio)-2-(β-epithiopropylthiomethyl)-3-thiapentane, 1,5-bis(β-epithiopropylthio)-2,4-bis(β-epithiopropylthiomethyl)-3-thiapentane, 1-(β-epithiopropylthio)-2,2-bis(β-epithiopropylthiomethyl)-4-thiahexane, 1,5,6-tris(β-epithiopropylthio)-4-(β-epithiopropylthiomethyl)-3-thiahexane, 1,8-bis(β-epithiopropylthio)-4-(β-epithiopropylthiomethyl)-3,6-dithiaoctane, 1,8-bis(β-epithiopropylthio)-4,5-bis(β-epithiopropylthiomethyl)-3,6-dithiaoctane, 1,8-bis(β-epithiopropylthio)-4,4-bis(β-epithiopropylthiomethyl)-3,6-dithiaoctane, 1,8-bis(β-epithiopropylthio)-2,4,5-tris(β-epithiopropylthiomethyl)-3,6-dithiaoctane, 1,8-bis(β-epithiopropylthio)-2,5-bis(β-epithiopropylthiomethyl)-3,6-dithiaoctane, 1,9-bis(β-epithiopropylthio)-5-(β-epithiopropylthiomethyl)-5-[(2-β-epithiopropylthioethyl)thiomethyl]-3,7-dithianonane, 1,10-bis(β-epithiopropylthio)-5,6-bis[(2-β-epithiopropylthioethyl)thio]-3,6,9-trithiadecane, 1,11-bis(β-epithiopropylthio)-4,8-bis(β-epithiopropylthiomethyl)-3,6,9-trithiaundecane, 1,11-bis(β-epithiopropylthio)-5,7-bis(β-epithiopropylthiomethyl)-3,6,9-trithiaundecane, and 1,11-bis(β-epithiopropylthio)-5,7-[(2-β-epithiopropylthioethyl)thiomethyl]-3,6,9-trithiaundecane, 1,11-bis(β-epithiopropylthio)-4,7-bis(β-epithiopropylthiomethyl)-3,6,9-trithiaundecane, and compounds derived therefrom by substituting at least one hydrogen of the episulfide group with a methyl group; alicyclic organic compounds such as 1,3- and 1,4-bis(β-epithiopropylthio)cyclohexanes, 1,3- and 1,4-bis(β-epithiopropylthiomethyl)cyclohexanes, bis[4-(β-epithiopropylthio)cyclohexyl]methane, 2,2-bis[4-(β-epithiopropylthio)cyclohexyl]propane, bis[4-(β-epithiopropylthio)cyclohexyl] sulfide, 2,5-bis(β-epithiopropylthiomethyl)-1,4-dithiane, and 2,5-bis(β-epithiopropylthioethylthiomethyl)-1,4-dithiane, and compounds derived therefrom by substituting at least one hydrogen of the episulfide group therein with a methyl group; and aromatic organic compounds such as 1,3- and 1,4-bis(β-epithiopropylthio)benzenes, 1,3- and 1,4-bis(β-epithiopropylthiomethyl)benzenes, bis[4-(β-epithiopropylthio)phenyl]methane, 2,2-bis[4-(β-epithiopropylthio)phenyl]propane, bis[4-(β-epithiopropylthio)phenyl] sulfide, bis[4-(β-epithiopropylthio)phenyl] sulfone, and 4,4'-bis(β-epithiopropylthio)biphenyl, and compounds derived therefrom by substituting at least one hydrogen of the episulfide group with a methyl group. They may be used herein either singly or in admixture of two or more thereof. The amount to be used is generally from 0.01 to 50 mole % of the total amount of the episulfide compound represented by the general formula (1).

Examples of the optional epoxy compounds are phenolic epoxy compounds produced through condensation of polyhydric phenol compounds, such as hydroquinone, catechol, resorcinol, bisphenol A, bisphenol F, bisphenol sulfone, bisphenol ether, bisphenol sulfide, bisphenol A halides, and novolak resin, with epihalohydrins; alcoholic epoxy compounds produced through condensation of polyhydric alcohol compounds, such as ethylene glycol, diethylene glycol, triethylene glycol, polyethylene glycol, propylene glycol, dipropylene glycol, polypropylene glycol, 1,3-propanediol, 1,4-butanediol, 1,6-hexanediol, neopentyl glycol, glycerin, trimethylolpropane trimethacrylate, pentaerythritol, 1,3- and 1,4-cyclohexanediols, 1,3- and 1,4-cyclohexanedimethanols, hydrogenated bisphenol A, bisphenol A-ethylene oxide adduct, and bisphenol A-propylene oxide adduct, with epihalohydrins; glycidyl ester-based epoxy compounds produced through condensation of polyhydric carboxylic acid compounds, such as adipic acid, sebacic acid, decanedicarboxylic acid, dimer acids, phthalic acid, isophthalic acid, terephthalic acid, tetrahydrophthalic acid, methyltetrahydrophthalic acid, hexahydrophthalic acid, hexahydroisophthalic acid, hexahydroterephthalic acid, hexachloroendomethylene tetrahydrophthalic ("HET") acid, nadic acid, maleic acid, succinic acid, fumaric acid, trimellitic acid, benzenetetracarboxylic acid, benzophenonetetracarboxylic acid, naphthalenedicarboxylic acid, and diphenyldicarboxylic acid, with epihalohydrins; amine-based epoxy compounds produced through condensation of primary amines, such as ethylenediamine, 1,2-diaminopropane, 1,3-diaminopropane, 1,2-diaminobutane, 1,3-diaminobutane, 1,4-diaminobutane, 1,5-diaminopentane, 1,6-diaminohexane, 1,7-diaminoheptane, 1,8-diaminooctane, bis(3-aminopropyl) ether, 1,2-bis(3-aminopropoxy)ethane, 1,3-bis(3-aminopropoxy)-2,2'-dimethylpropane, 1,2-, 1,3- and 1,4-bisaminocyclohexanes, 1,3- and 1,4-bisaminomethylcyclohexanes, 1,3- and 1,4-bisaminoethylcyclohexanes, 1,3- and 1,4-bisaminopropylcyclohexanes, hydrogenated 4,4'-diaminodiphenylmethane, isophoronediamine, 1,4-bisaminopropylpiperazine, m- and p-phenylenediamines, 2,4- and 2,6-tolylenediamine, m- and p-xylylenediamines, 1,5- and 2,6-naphthalenediamines, 4,4'-diaminodiphenylmethane, 4,4'-diaminodiphenyl ether, and 2,2-(4,4'-diaminodiphenyl)propane, or secondary amines, such as N,N'-dimethylethylenediamine, N,N'-dimethyl-1,2-diaminopropane, N,N'-dimethyl-1,3-diaminopropane, N,N'-dimethyl-1,2-diaminobutane, N,N'-dimethyl-1,3-diaminobutane, N,N'-dimethyl-1,4-diaminobutane, N,N'-dimethyl-1,5-diaminopentane, N,N'-dimethyl-1,6-diaminohexane, N,N'-dimethyl-1,7-diaminoheptane, N,N'-diethylethylenediamine, N,N'-diethyl-1,2-diaminopropane, N,N'-diethyl-1,3-diaminopropane, N,N'-diethyl-1,2-diaminobutane, N,N'-diethyl-1,3-diaminobutane, N,N'-diethyl-1,4-diaminobutane, N,N'-diethyl-1,6-diaminohexane, piperazine, 2-methylpiperazine, 2,5- and 2,6-dimethylpiperazines, homopiperazine, 1,1-di(4-piperidyl)methane, 1,2-di(4-piperidyl)ethane, 1,3-di(4-piperidyl)propane, and 1,4-di(4-piperidyl)butane, with epihalohydrins; alicyclic epoxy compounds such as 3,4-epoxycyclohexyl 3,4-epoxycyclohexanecarboxylate, vinylcyclohexane dioxide, 2-(3,4-epoxycyclohexyl)-5,5-spiro-3,4-epoxycyclohexanemetadioxane, and bis(3,4-epoxycyclohexyl) adipate; epoxy compounds produced through epoxydation of unsaturated compounds, such as cyclopentadiene epoxide, epoxidated soybean oil, epoxydated polybutadiene, and vinylcyclohexene epoxide; and urethane-based epoxy compounds obtained from the above-mentioned polyhydric alcohols or phenolic compounds with diisocyanates and glycidols. They may be used herein either singly or in admixture of two or more thereof. The amount to be used is generally from 0.01 to 50 mole % of the total amount of the episulfide compound represented by the general formula (1).

Examples of the optional, homopolymerizable vinyl monomers are compounds having an ester structure of acrylic or methacrylic acid with a monohydric or polyhydric alcohol, such as methyl acrylate, methyl methacrylate, ethyl acrylate, ethyl methacrylate, ethylene glycol diacrylate, ethylene glycol dimethacrylate, diethylene glycol diacrylate, diethylene glycol dimethacrylate, triethylene glycol diacrylate, triethylene glycol dimethacrylate, polyethylene glycol diacrylate, polyethylene glycol dimethacrylate, 1,3-butylene glycol diacrylate, 1,3-butylene glycol dimethacrylate, 1,6-hexanediol diacrylate, 1,6-hexanediol dimethacrylate, neopentyl glycol diacrylate, neopentyl glycol dimethacrylate, polypropylene glycol diacrylate, polypropylene glycol dimethacrylate, 2,2-bis[4-(acryloxyethoxy)phenyl]propane, 2,2-bis[4-(methacryloxyethoxy)phenyl]propane, 2,2-bis[4-(acryloxydiethoxy)phenyl]propane, 2,2-bis[4-(methacryloxydiethoxy)phenyl]propane, 2,2-bis[4-(acryloxypolyethoxy)phenyl]propane, 2,2-bis[4-(methacryloxypolyethoxy)phenyl]propane, trimethylolpropane triacrylate, trimethylol propane trimethacrylate, pentaerythritol tetraacrylate, pentaerythritol tetramethacrylate, bis(2,2,2-trimethylolethyl) ether hexaacrylate, and bis(2,2,2-trimethylolethyl) ether hexamethacrylate; allyl compounds such as allyl sulfide, diallyl phthalate, and diethylene glycol bisallylcarbonate; vinyl compounds such as acrolein, acrylonitrile, and vinyl sulfide; and aromatic vinyl compounds such as styrene, α-methylstyrene, methylvinylbenzene, ethylvinylbenzene, α-chlorostyrene, chlorovinylbenzene, vinylbenzyl chloride, paradivinylbenzene, and metadivinylbenzene. They may be used herein either singly or in admixture of two or more thereof. The amount to be used is generally from 0.01 to 20 mole % of the total amount of the episulfide compound represented by the general formula (1).

To the polymerizable composition that comprises the above-mentioned episulfide compound represented by the general formula (1) and optional components, if desired, is optionally added other additives, such as UV absorbent, antioxidant, discoloration inhibitor, and fluorescent dye for improving the weather resistance of the resulting polymers. Also if desired, catalysts may be used for improving the polymerization reactivity. Examples of the catalysts include, for example, amines, phosphines, quaternary ammonium salts, quaternary phosphonium salts, tertiary sulfonium salts, secondary iodonium salts, mineral acids, Lewis acids, organic acids, silicic acids, and tetrafluoroboric acid.

Using the episulfide compounds of the invention, optical materials can be produced, for example, according to the method mentioned below.

A uniform composition containing the above-mentioned polymerizable composition and other optional additives is first prepared, and this is cast into a glass or metal mold combined with a resin gasket, and heated and cured therein, according to a method of casting polymerization. If desired, the mold may be subjected to mold release or a mold releasing agent may be added to the composition, for facilitating good release of the molded resin from the mold. The polymerization temperature varies depending on the compounds to be used, but is generally from −20° C. to +150° C.; and the polymerization time is from about 0.5 to 72 hours. After having been thus polymerized and released from the mold, the polymer may be readily colored with an ordinary disperse dye in water or in an organic solvent. For facilitating the dyeing, a carrier may be added to the dye dispersion, or the dyeing bath may be heated. Though not limited thereto, the thus-obtained optical materials are especially favorable for optical products such as plastic lenses.

The episulfide compounds of the invention have three, episulfide group-containing reactive substituents bonded to the center trithiane ring, and are favorable for starting materials for optical materials. The optical materials obtained by using the episulfide compounds of the invention have a high refractive index and a high Abbe's number, and have excellent heat resistance and transparency. Therefore, they are suitable for materials for optical products, for example, for lenses such as those for spectacles and cameras, and also for prisms, optical fibers, substrates for recording media such as optical discs and magnetic discs, as well as for color filters, IR-absorbing filters, etc.

EXAMPLES

The invention is described more concretely with reference to the following Examples, which, however, are not intended to restrict the scope of the invention. The physical properties of the episulfide compounds obtained in the Examples, and those of the polymers obtained in the following Application Examples and Comparative Application Examples were measured according to the methods mentioned below.
Physical Properties of the Episulfide Compounds
The refractive index ($n_D$) and the Abbe's number ($v_D$) were measured at 25° C. with an Abbe's refractometer, DR-M4 manufactured by Atago Co., Ltd.
Physical Properties of Polymers
Refractive index ($n_D$) and Abbe's number ($v_D$): Measured in the same manner as above.
Appearance: Visually checked.
Heat resistance: Measured with a TMA analyzer manufactured by Rigaku International Corporation. Concretely, using a pin having a diameter of 0.5 mm, TMA of each sample was measured under a load of 98 mN (10 gf) at a heating rate of 10° C./min. From the peak temperature appearing in the chart, the heat resistance of the sample was evaluated.
Transparency: Using a UV spectrometer, UV-330 manufactured by Hitachi, Ltd., the 550 nm UV transmittance was measured, from which the transparency was evaluated.

Example 1
Production example of 2,4,6-tris(epithiomethylthiomethyl)-1,3,5-trithiane (T1) (the general formula (1) wherein n is 0)

70 wt. % (v/v) sulfuric acid (100 ml) was bubbled with hydrogen sulfide for 30 minutes at 0° C., to which was dropwise added 40 wt. % chloroacetaldehyde (17.5 ml) at 0° C. over 7.5 hours. Still at the temperature, this was further bubbled with hydrogen sulfide for 24 hours. The aqueous solution of the upper layer was removed through decantation, and the residue soluble in dichloromethane (150 ml) was washed with water (25 ml×3 times), dried over anhydrous magnesium sulfate, and filtered. The solvent was evaporated away, and a pale yellow crude product (9.5 g) was obtained. The crude product was washed with hexane (40 ml×4 times), hexane/ether (6/1) (50 ml×2 times) and hot hexane (30 ml×2 times), and dried in vacuum to obtain a white crystal, 2,4,6-tris(chloromethyl)-1,3,5-trithiane (2.50 g). To a methanol (25 ml) solution of this compound (0.3 g, 1.06 mmoles) was added a methanol solution (5 ml) of potassium hydroxide (0.62 g, 11 mmoles) all at a time with vigorous stirring at room temperature, and this was further stirred at room temperature for 75 minutes. The reaction mixture was diluted with water (30 ml), and extracted with dichloromethane (20 ml×5 times), and the resulting extract was dried over anhydrous magnesium sulfate and filtered. The solvent was evaporated away from the filtrate, and a yellow oily residue, 2,4,6-trimethylene-1,3,5-trithiane, (150 mg) was thus obtained. To a benzene (1 ml) solution of this compound (0.47 g) were added 3-mercaptopropene sulfide (1.14 g) and azobisbutyronitrile (0.2 mg), and the mixture was stirred in an argon atmosphere at 40° C. for 2 hours. The solvent was evaporated away from the reaction mixture, and the resulting residue was recrystallized from chloroform/methanol to obtain a crystal of 2,4,6-tris(epithiomethylthiomethyl)-1,3,5-trithiane (411 mg) (m.p. =55 to 56° C.).

For identifying its structure, the compound was analyzed and its data are shown below.

$^1$H-NMR (solvent, CDCl$_3$; internal standard substance, TMS): δ2.27 (d, 3H), δ2.59 (d, 3H), δ2.76 (m, 3H), δ3.19-3.29 (m, 12H), δ4.37-4.63 (t,t,m, 3H).

IR (KBr tablet): 620, 660, 710, 740, 800, 860, 920, 1060, 1095, 1190, 1250, 1420, 1440 cm$^{-1}$.

Example 2
Production example of 2,4,6-tris(epithiopropylthiomethyl)-1,3,5-trithiane (T3) (the general formula (1) wherein n is 2)

2,4,6-Tris(epithiopropylthiomethyl)-1,3,5-trithiane (T3) (481 mg) was obtained in the same manner as in Example 1, except that 5-mercaptopentene sulfide (1.45 mg) and cyclohexylcarbonyl peroxide (0.3 mg) were used in place of 3-mercaptopropene sulfide and azobisbutyronitrile, respectively. Its refractive index (n$_D$) was 1.696, and its Abbe's number (ν$_D$) was 30.1.

For identifying its structure, the compound was analyzed and its data are shown below.

$^1$H-NMR (solvent, CDCl$_3$; internal standard substance, TMS): δ2.29 (d, 3H), δ2.44-2.52 (m, 12H), δ2.58 (d, 3H), δ2.74 (m, 3H), δ3.12-3.16 (m, 6H), δ3.25-3.31 (m, 6H), δ4.39-4.66 (t,t,m, 3H).

IR (KBr tablet): 620, 658, 714, 738, 803, 861, 918, 1064, 1099, 1185, 1244, 1444, 1446 cm$^{-1}$.

Application Example 1
Production of Optical Material Made of Polymer

A mixture of T1 (0.05 moles) obtained in Example 1 and 2×10$^{-5}$ moles of a polymerization catalyst, tetra(n-butyl) phosphonium bromide (CT1), was uniformly stirred at 60° C., and cast into a mold of two glass sheets for lens production. In the mold, the mixture was polymerized under heat at 70° C. for 10 hours, then at 80° C. for 5 hours and then at 100° C. for 3 hours to obtain a lens-shaped polymer. The physical properties of the thus-obtained polymer are given in Table 1. As shown in Table 1, the polymer obtained in this Application Example 1 was colorless and transparent. Its refractive index (n$_D$) was extremely high, i.e., 1.796; its Abbe's number (ν$_D$) was also high, i.e., 30 (this means low dispersiveness of the polymer); and its heat resistance (135° C.) and transparency (92%) were excellent. Accordingly, the polymer obtained was favorable to optical materials.

Application Examples 2 to 5
Production of Optical Material Made of Polymer

Lens-shaped polymers were produced in the same manner as in Application Example 1, except that the episulfide compound (C1 component) of the invention, another episulfide compound, epoxy compound and/or vinyl monomer (C2 component), and the polymerization catalyst as shown in Table 1 were used, and the polymerization condition was suitably varied. See also definitions of abbreviations that follow Table 1. Their physical properties are given in Table 1. As shown in Table 1, the polymers obtained in Application Examples 2 to 5 were also colorless and transparent. Their refractive index (n$_D$) was extremely high, i.e., from 1.709 to 1.778; their Abbe's number (ν$_D$) was also high, i.e., from 31 to 36 (this means low dispersiveness of the polymers); and their heat resistance (111 to 141° C.) and transparency (89 to 96%) were excellent.

Comparative Application Example 1
Production of Optical Material Made of Polymer As shown in Table 1, a mixture of 0.1 moles of pentaerythritol tetrakismercaptopropionate (CE5), 0.2 moles of m-xylylene diisocyanate (CE6), and 1.0×10$^{-4}$ moles of dibutyltin dichloride (CT5) was uniformly stirred, and cast into a mold of two glass sheets for lens production. In the mold, the mixture was polymerized under heat at 50° C. for 10 hours, then at 60° C. for 5 hours and then at 120° C. for 3 hours to obtain a lens-shaped polymer. The physical properties of the thus-obtained polymer are given in Table 1. As shown in Table 1, the polymer obtained in this Comparative Application Example 1 was colorless and transparent (92%), but its n$_D$/ν$_D$ was 1.59/36, or that is, its refractive index was low. In addition, its heat resistance (86° C.) was inferior.

Comparative Application Examples 2 and 3
Production of Optical Material Made of Polymer Lens-shaped polymers were produced in the same manner as in Comparative Application Example 1, except that the materials as shown in Table 1 were used. Their physical properties are given in Table 1. As shown in Table 1, the polymer of Comparative Application Example 2 had an n$_D$/ν$_D$ of 1.67/28, or that is, its n$_D$ and ν$_D$ were both low. Though its heat resistance (94° C.) was relatively good, it was discolored and its transparency (81%) was low. The polymer of Comparative Application Example 3 had a relatively high ν$_D$ of 36, it had good weather resistance, and it was colorless and transparent (89%). However, its heat resistance (90° C.) was not good, its n$_D$ was not so high, i.e., 1.70, and it was brittle.

TABLE 1

| Application Example No. | Component C1 (mole) | Component C2 (mole) | Polymerization catalyst (mole) | n$_D$/ν$_D$ | Appearance | Heat resistance (° C.) | Transparency (%) |
|---|---|---|---|---|---|---|---|
| 1 | T1 (0.05) | — | CT1 (2 × 10$^{-5}$) | 1.796/30 | Colorless and transparent Hard | 135 | 92 |
| 2 | T2 (0.04) | CE1 (0.01) | CT2 (1.8 × 10$^{-5}$) | 1.766/32 | Colorless and transparent Hard | 111 | 96 |

TABLE 1-continued

| Application Example No. | Component C1 (mole) | Component C2 (mole) | Polymerization catalyst (mole) | $\eta_D/\nu_D$ | Appearance | Heat resistance (°C.) | Transparency (%) |
|---|---|---|---|---|---|---|---|
| 3 | T3 (0.047) | CE2 (0.003) | CT3 (3.9 × 10⁻⁴) | 1.746/35 | Colorless and transparent Hard | 141 | 91 |
| 4 | T1 (0.035) | CE3 (0.015) | CT3 (3.1 × 10⁻⁴) | 1.709/36 | Colorless and transparent Hard | 138 | 90 |
| 5 | T1/T3 (0.03/ 0.013) | CE4 (0.0075) | CT4 (9 × 10⁻⁵) | 1.778/31 | Colorless and transparent Hard | 115 | 89 |
| Comparative Application Example No. | Starting formulation (mole) | | Polymerization catalyst (mole) | $\eta_D/\nu_D$ | Appearance | Heat resistance (°C.) | Transparency (%) |
| 1 | CE5/CE6 (0.1/0.2) | | CT5 (1.0 × 10⁻⁴) | 1.59/36 | Colorless and transparent Hard | 86 | 92 |
| 2 | CE7/CE6 (0.2/0.3) | | CT5 (1.5 × 10⁻⁴) | 1.67/28 | Pale yellow and transparent Hard | 94 | 81 |
| 3 | CE1 (0.1) | | CT2 (1.0 × 10⁻⁴) | 1.70/36 | Colorless and transparent Brittle | 90 | 89 |

Abbreviations in Table 1

T1: 2,4,6-Tris(epithiomethylthiomethyl)-1,3,5-trithiane
T2: 2,4,6-Tris(epithioethylthiomethyl)-1,3,5-trithiane
T3: 2,4,6-Tris(epithiopropylthiomethyl)-1,3,5-trithiane
CE1: Bis(epithiomethyl) sulfide
CE2: 2,2-Bis(4-(2-glycidyloxy)ethoxyphenyl)propane
CE3: Cyclohexene oxide
CE4: Bis(2-acryloxyethyl) 1,4-xylylcarbamate
CE5: Pentaerythritol tetrakismercaptopropionate
CE6: m-Xylylene diisocyanate
CE7: 1,3,5-Trimercaptobenzene
CT1: Tetra(n-butyl)phosphonium bromide
CT2: Triethylamine
CT3: 2,4,6-Tridimethylaminophenol
CT4: Boron trifluoride/pyridine complex
CT5: Dibutyltin dichloride While the invention has been described in connection with certain embodiments so that aspects thereof may be more fully understood and appreciated, it is not intended to limit the invention to these particular embodiments. On the contrary, it is intended to cover all alternatives, modifications and equivalents as may be included within the scope of the invention as defined by the appended claims.

What is claimed is:

1. An episulfide compound represented by the general formula (1):

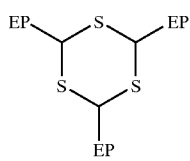
(1)

wherein EP represents

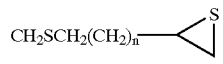

and n is an integer of from 0 to 2.

2. The episulfide compound of claim 1, wherein the episulfide compound represented by the general formula (1) is 2,4,6-tris(epithiomethylthiomethyl)-1,3,5-trithiane, 2,4,6-tris(epithioethylthiomethyl)-1,3,5-trithiane, or 2,4,6-tris (epithiopropylthiomethyl)-1,3,5-trithiane.

3. A method for producing an episulfide compound represented by the general formula (1):

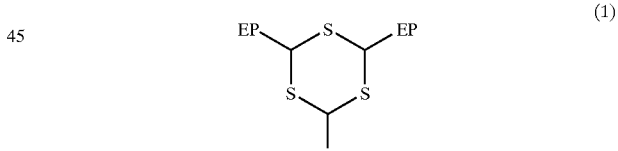
(1)

wherein EP represents

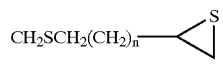

and n is an integer of from 0 to 2, wherein the method comprises reacting a mercapto group-containing episulfide compound with 2,4,6-trimethylene-1,3,5-trithiane.

4. The method for producing an episulfide compound of claim 3, wherein the mercapto group-containing episulfide compound is 3-mercaptopropene sulfide, 4-mercaptobutene sulfide, or 5-mercaptopentene sulfide.

5. The method for producing an episulfide compound of claim 3, wherein the episulfide compound represented by the general formula (1) is 2,4,6-tris(epithiomethylthiomethyl)-

1,3,5-trithiane, 2,4,6-tris(epithioethylthiomethyl)-1,3,5-trithiane, or 2,4,6-tris(epithiopropylthiomethyl)-1,3,5-trithiane.

6. An optical product comprising a polymer obtained by using, as a monomer component, at least one episulfide compound represented by the general formula (1):

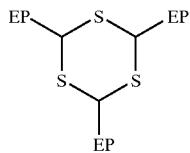
(1)

wherein EP represents

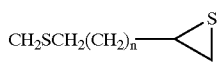

and n is an integer of from 0 to 2.

7. The optical product of claim 6, wherein the episulfide compound represented by the general formula (1) is 2,4,6-tris(epithiomethylthiomethyl)-1,3,5-trithiane, 2,4,6-tris(epithioethylthiomethyl)-1,3,5-trithiane, or 2,4,6-tris(epithiopropylthiomethyl)-1,3,5-trithiane.

8. The optical product of claim 6, wherein the polymer is obtained by using, as monomer components, the episulfide compound represented by the general formula (1) and another episulfide compound.

9. The optical product of claim 6, wherein the polymer is obtained by using, as monomer components, the episulfide compound represented by the general formula (1) and an epoxy compound.

10. The optical product of claim 6, wherein the polymer is obtained by using, as monomer components, the episulfide compound represented by the general formula (1) and a homopolymerizable vinyl monomer.

11. The optical product of claim 6, wherein the polymer is obtained by using, as monomer components, the episulfide compound represented by the general formula (1), a polythiol compound, and at least one of a polyisocyanate compound and a polyisothiocyanate compound.

12. The optical product of claim 6, wherein the optical product comprises a plastic lens.

13. The optical product of claim 7, wherein the optical product comprises a plastic lens.

14. The optical product of claim 8, wherein the optical product comprises a plastic lens.

15. The optical product of claim 9, wherein the optical product comprises a plastic lens.

16. The optical product of claim 10, wherein the optical product comprises a plastic lens.

17. The optical product of claim 11, wherein the optical product comprises a plastic lens.

* * * * *